US012036057B1

(12) United States Patent
Youn et al.

(10) Patent No.: US 12,036,057 B1
(45) Date of Patent: Jul. 16, 2024

(54) PORTABLE X-RAY DEVICE DRIVEN BY PFC-BASED INVERTER

(71) Applicants: FSK Co., Ltd., Gimpo-si (KR); Ju Seon Youn, Seoul (KR); Seung An Kwon, Seoul (KR); Young Il Yoo, Anyang-si (KR); Sang In Shim, Siheung-si (KR); Ha Yeon Youn, Seoul (KR); Sung Sup Kim, Chuncheon-si (KR); Ronald Viola, Pittsford, NY (US)

(72) Inventors: Ju Seon Youn, Seoul (KR); Seung An Kwon, Seoul (KR); Young Il Yoo, Anyang-si (KR); Sang In Shim, Siheung-si (KR); Ha Yeon Youn, Seoul (KR); Sung Sup Kim, Chuncheon-si (KR); Ronald Viola, Pittsford, NY (US)

(73) Assignee: FSK Co., Ltd., Gimpo-si (KR)

( * ) Notice: Subject to any disclaimer, the term of this patent is extended or adjusted under 35 U.S.C. 154(b) by 0 days.

(21) Appl. No.: 18/405,732

(22) Filed: Jan. 5, 2024

(30) Foreign Application Priority Data

Nov. 9, 2022 (KR) .......................... 10-2022-0148437

(51) Int. Cl.
*A61B 6/00* (2024.01)
(52) U.S. Cl.
CPC .......... *A61B 6/4405* (2013.01); *A61B 6/4452* (2013.01); *A61B 6/5258* (2013.01); *A61B 6/56* (2013.01)
(58) Field of Classification Search
CPC .................................................. A61B 6/4405
See application file for complete search history.

(56) References Cited

U.S. PATENT DOCUMENTS

2020/0329548 A1* 10/2020 Ishiyama ............. H02M 7/219
2023/0117579 A1* 4/2023 Steadman Booker ......................
A61B 6/4405
378/145

FOREIGN PATENT DOCUMENTS

JP 2015-181580 A 10/2015
KR 10-0935203 B1 1/2010
(Continued)

OTHER PUBLICATIONS

Korean Written Decision on Registration for KR 10-2022-0148437 dated Aug. 16, 2023.
(Continued)

*Primary Examiner* — Dani Fox
(74) *Attorney, Agent, or Firm* — Sughrue Mion, PLLC

(57) ABSTRACT

Provided is a portable X-ray device powered by a power factor correction (PFC)-based inverter, which includes a body in which a plurality of wheels are mounted on a lower surface, an input/output device which extends from an installation ground to a predetermined height and outputs data acquired from an X-ray photographing part is mounted on one side, and a handle with a structure gripped by a hand of a user is mounted on one side; a variable support which is mounted on an upper portion of the body by a hinge structure; an X-ray photographing part which is mounted on one end portion of the variable support; and a power supply mounted inside the body and provided with a PFC-based inverter configured to remove noise from applied commercial AC power, and provide the high DC voltage to the X-ray photographing part.

3 Claims, 13 Drawing Sheets

(56) References Cited

FOREIGN PATENT DOCUMENTS

| | | |
|---|---|---|
| KR | 10-2014-0089254 A | 7/2014 |
| KR | 10-2082458 B1 | 2/2020 |

OTHER PUBLICATIONS

Korean Notice of Final Rejection for KR 10-2022-0148437 dated Jun. 28, 2023.

* cited by examiner

[FIG. 1]
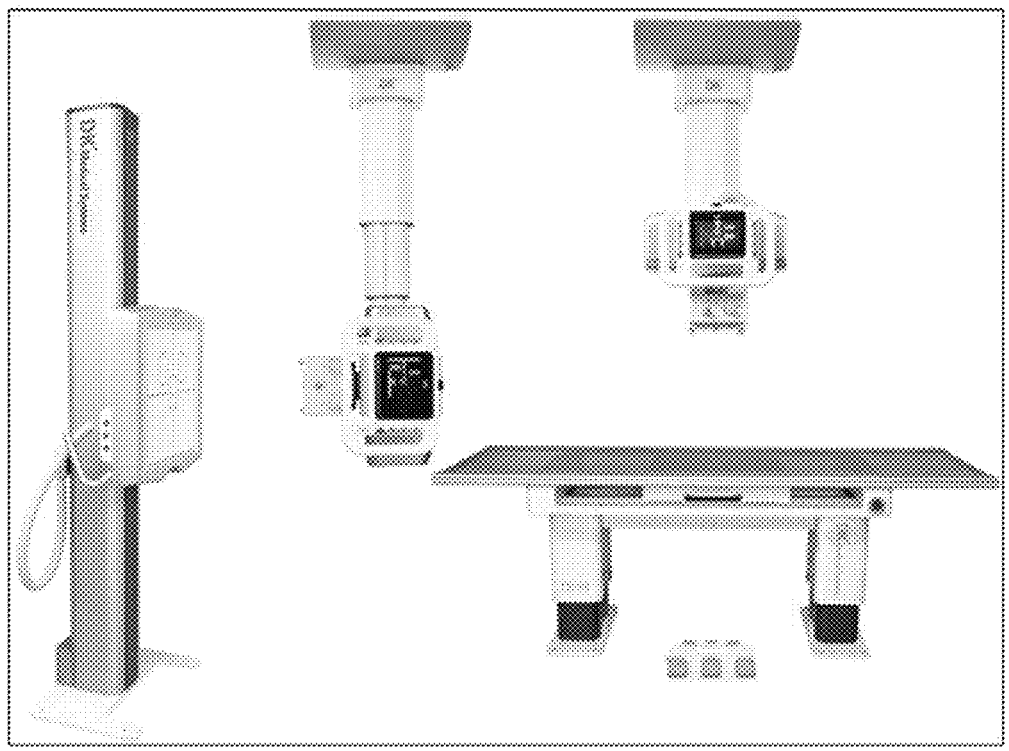

[FIG. 2]
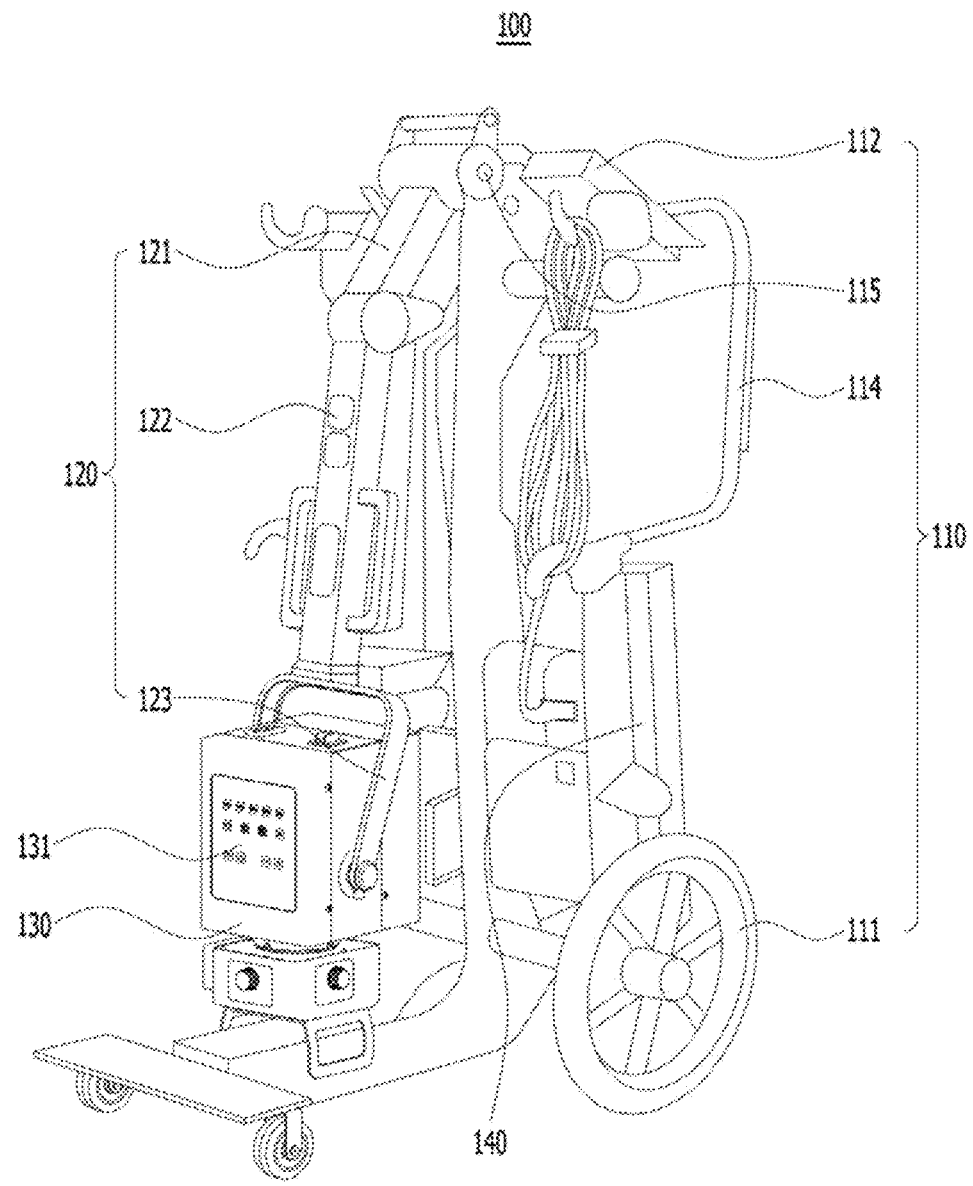

[FIG. 3]
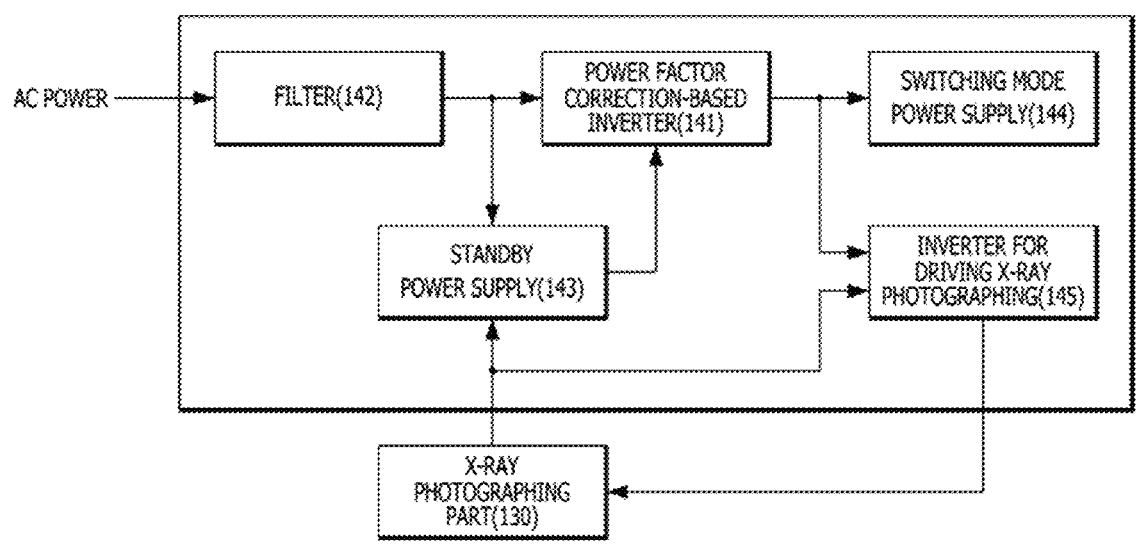

[FIG. 4]
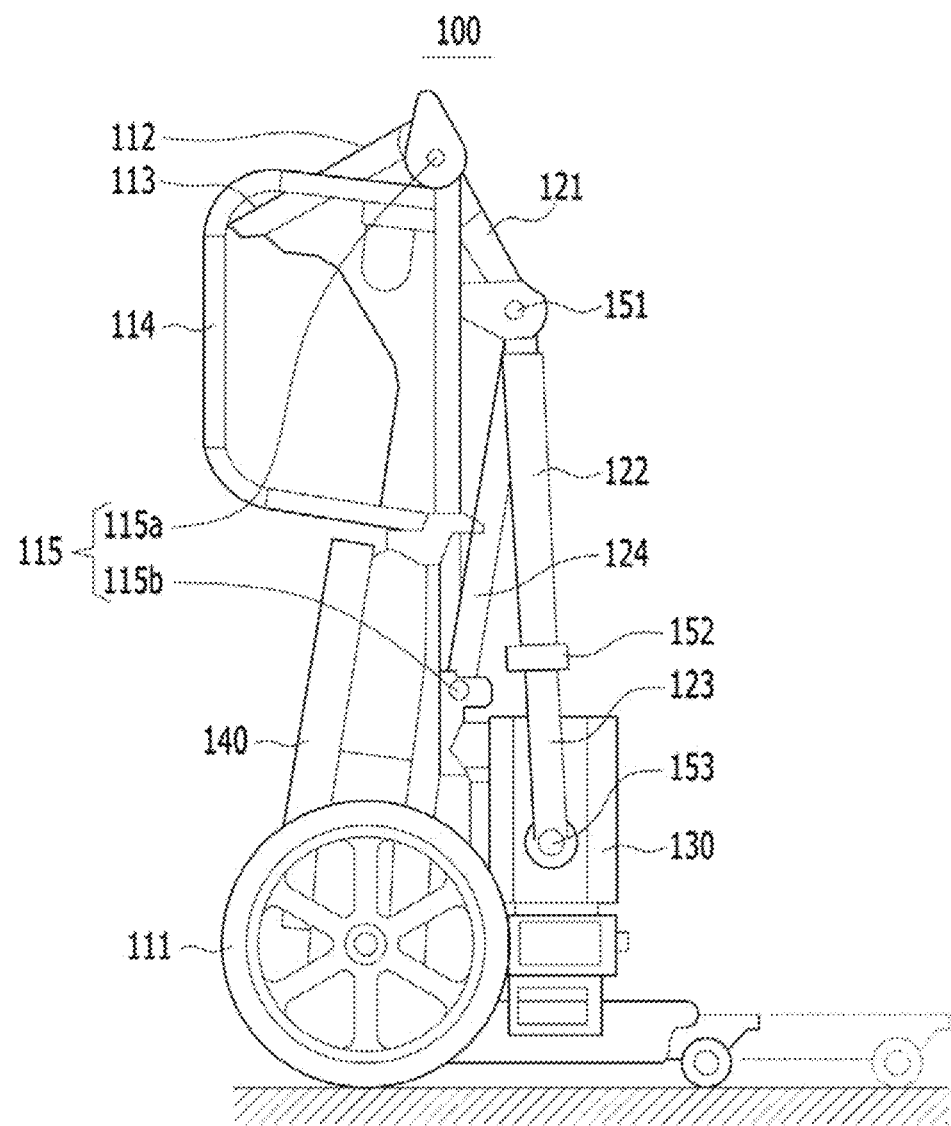

[FIG. 5]
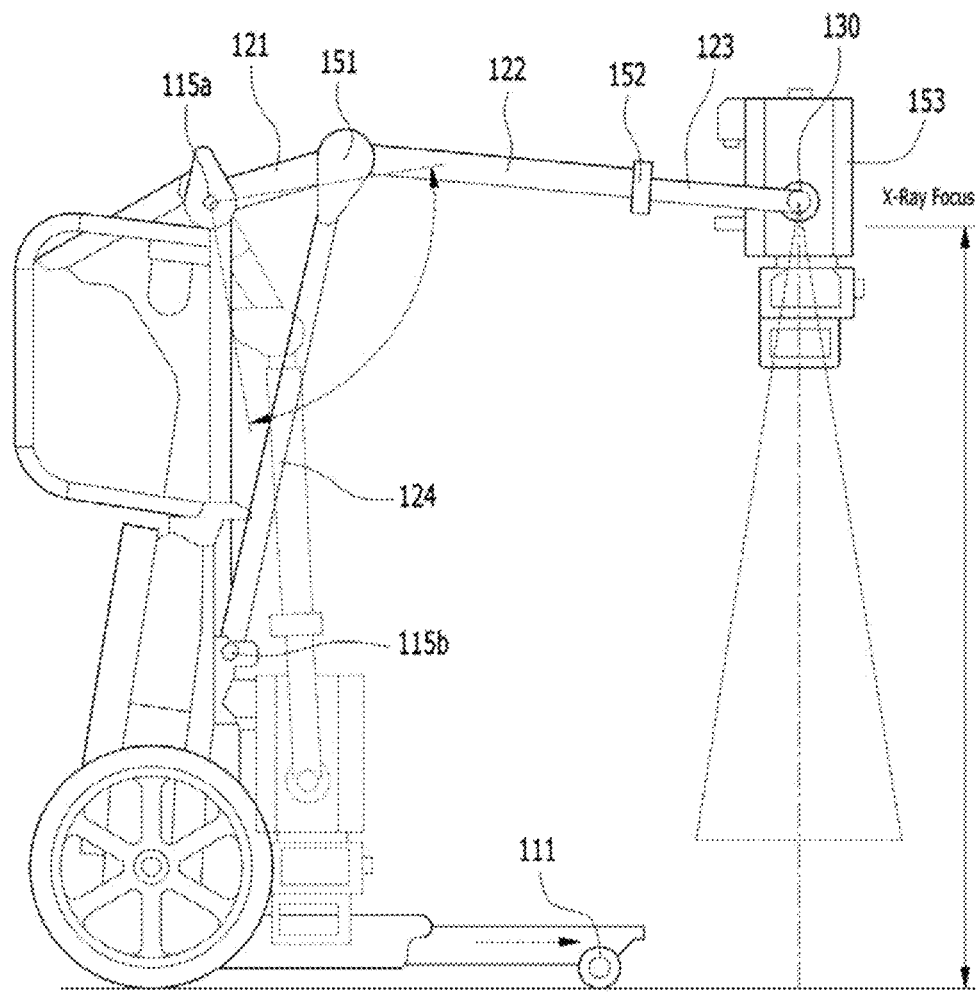

[FIG. 6]
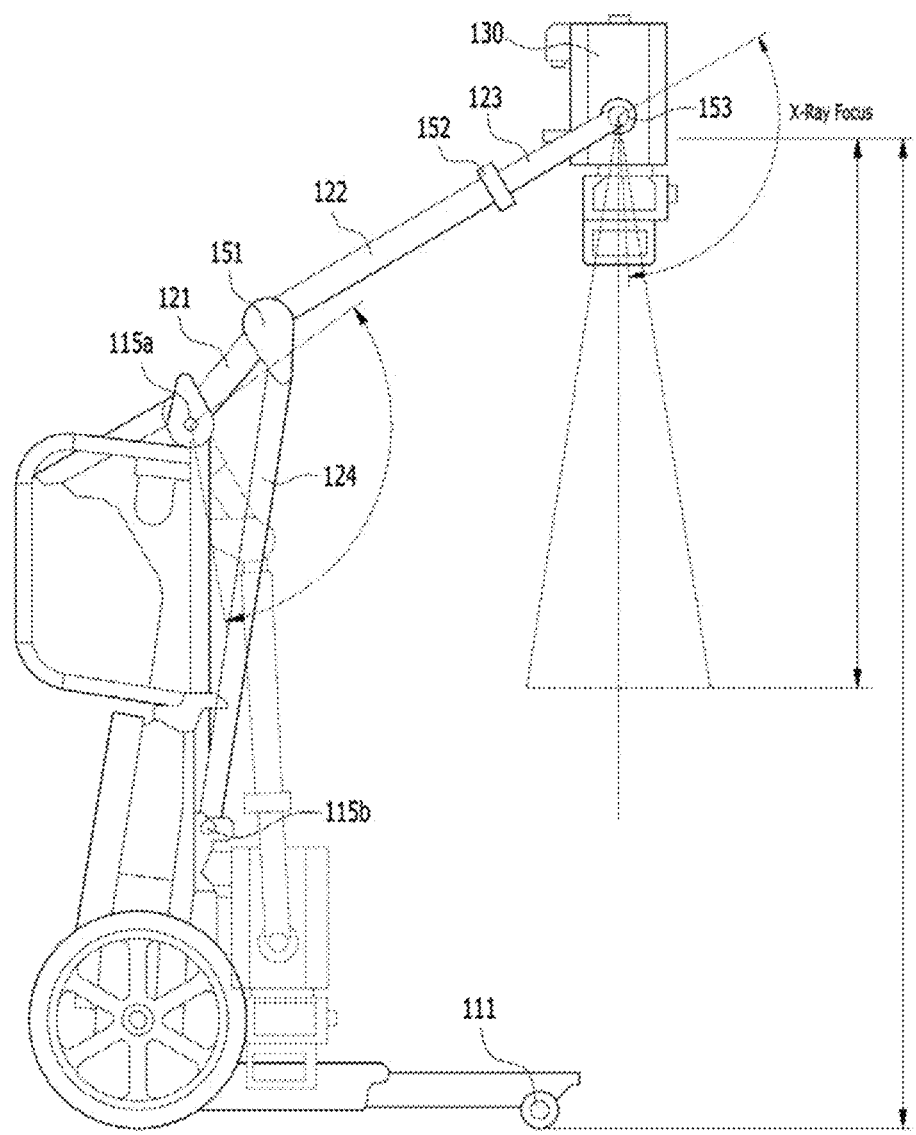

[FIG. 7]
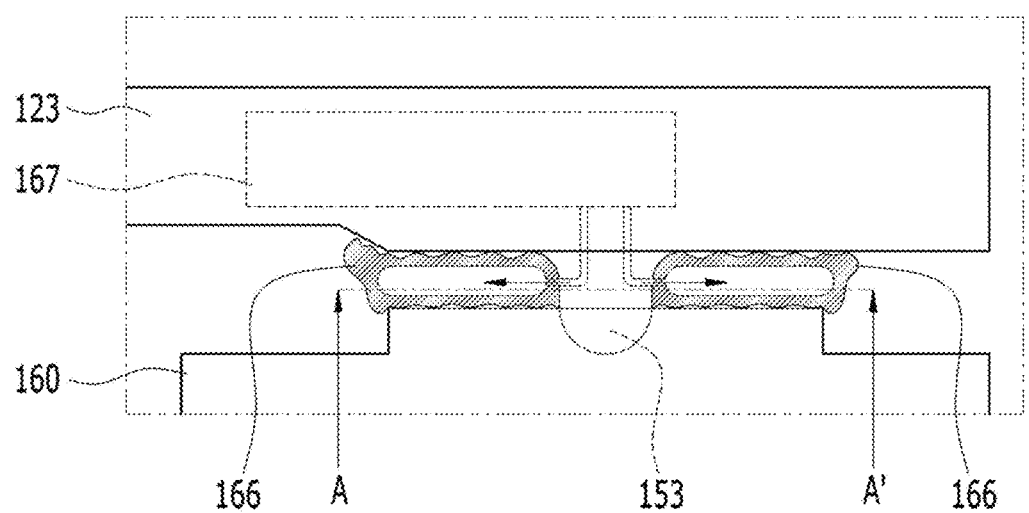

[FIG. 8]
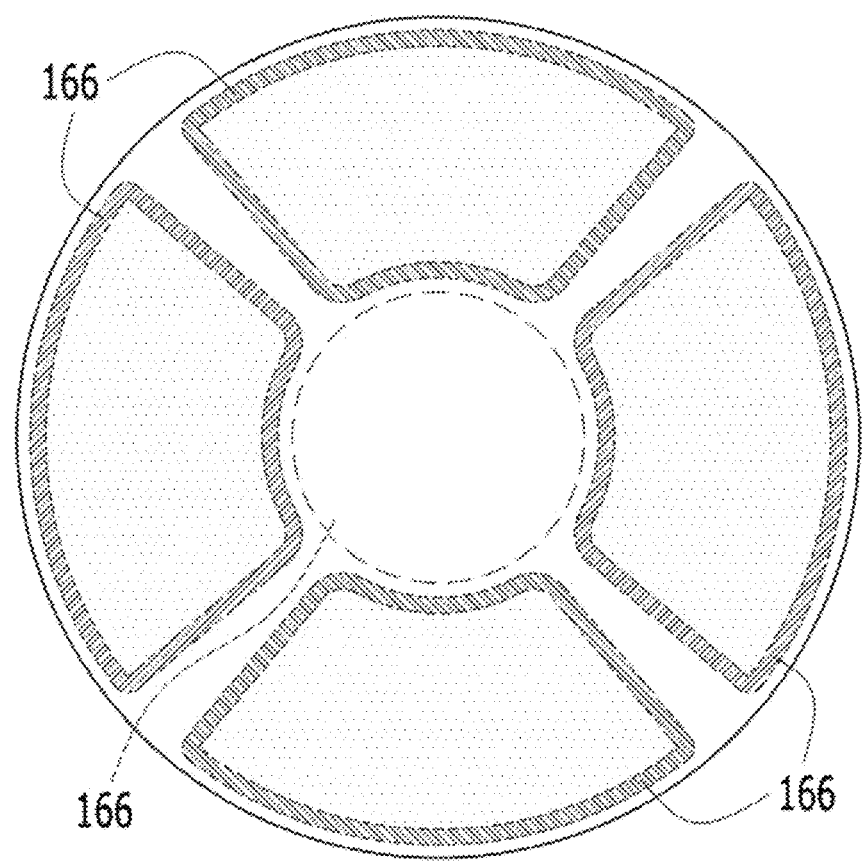

[FIG. 9]
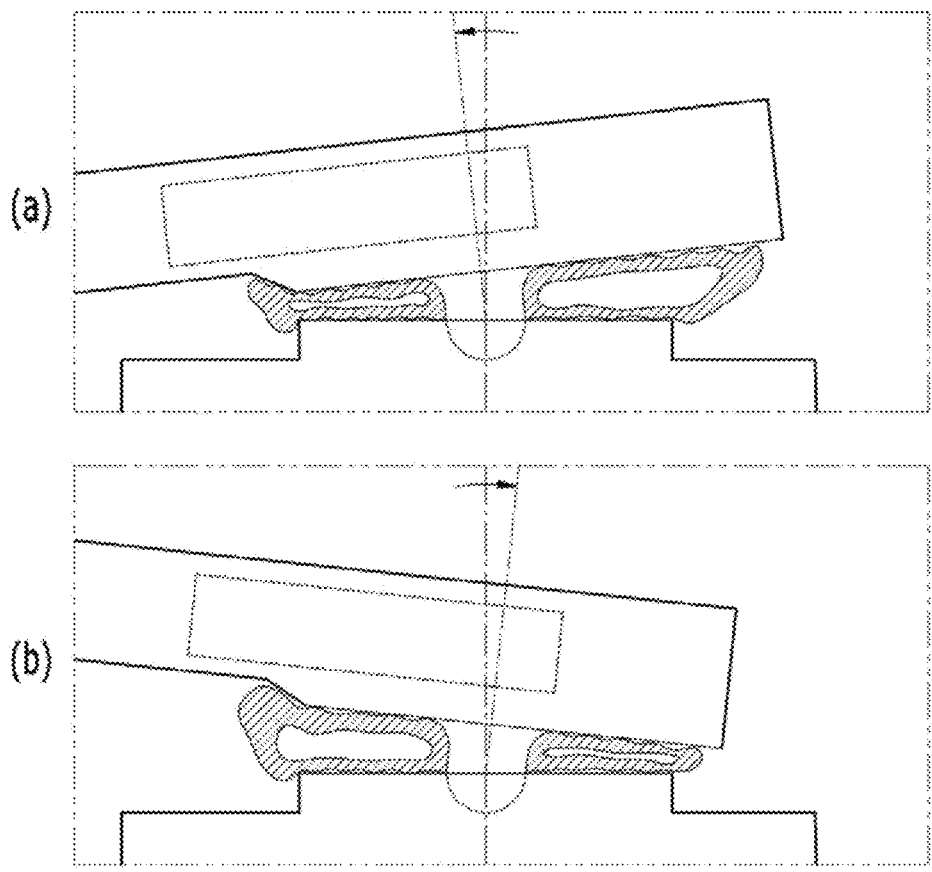

[FIG. 10]
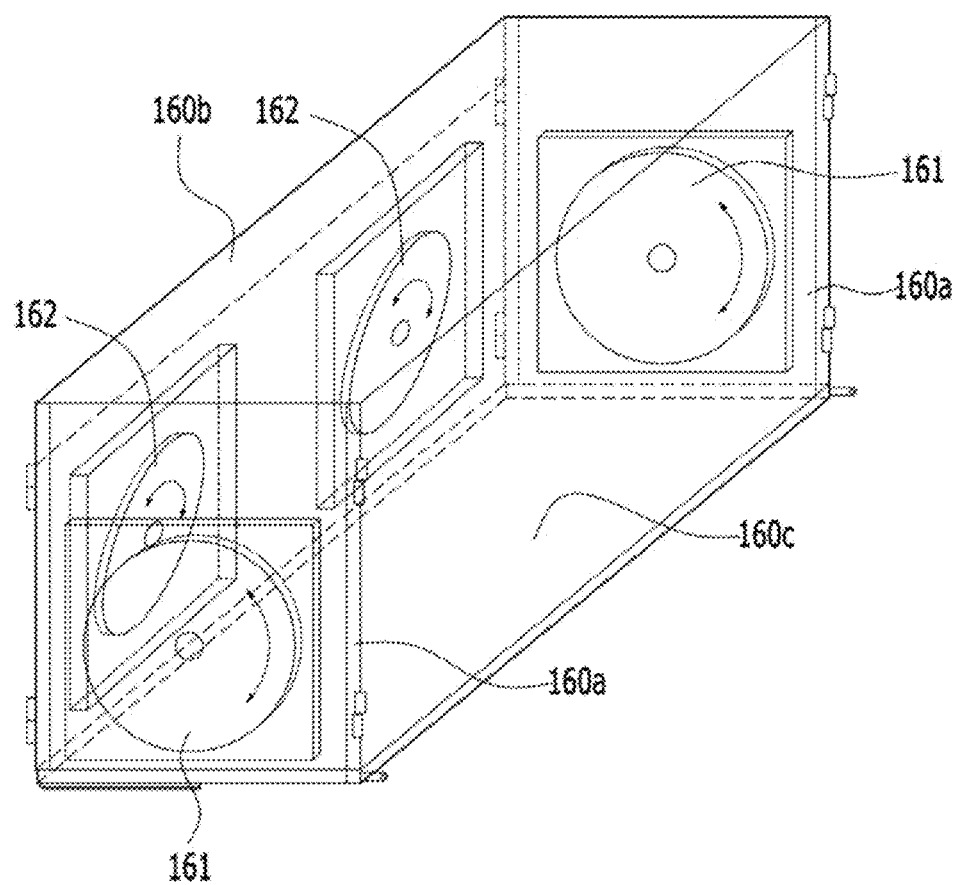

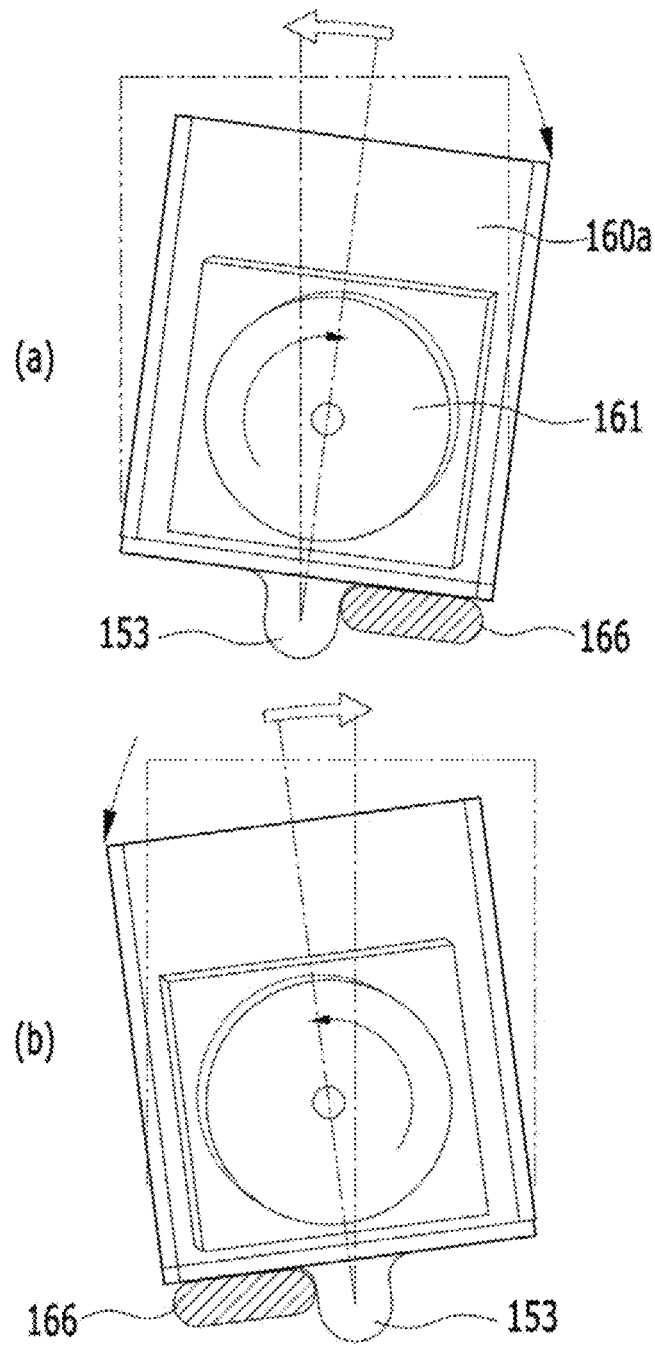
[FIG. 11]

[FIG. 12]
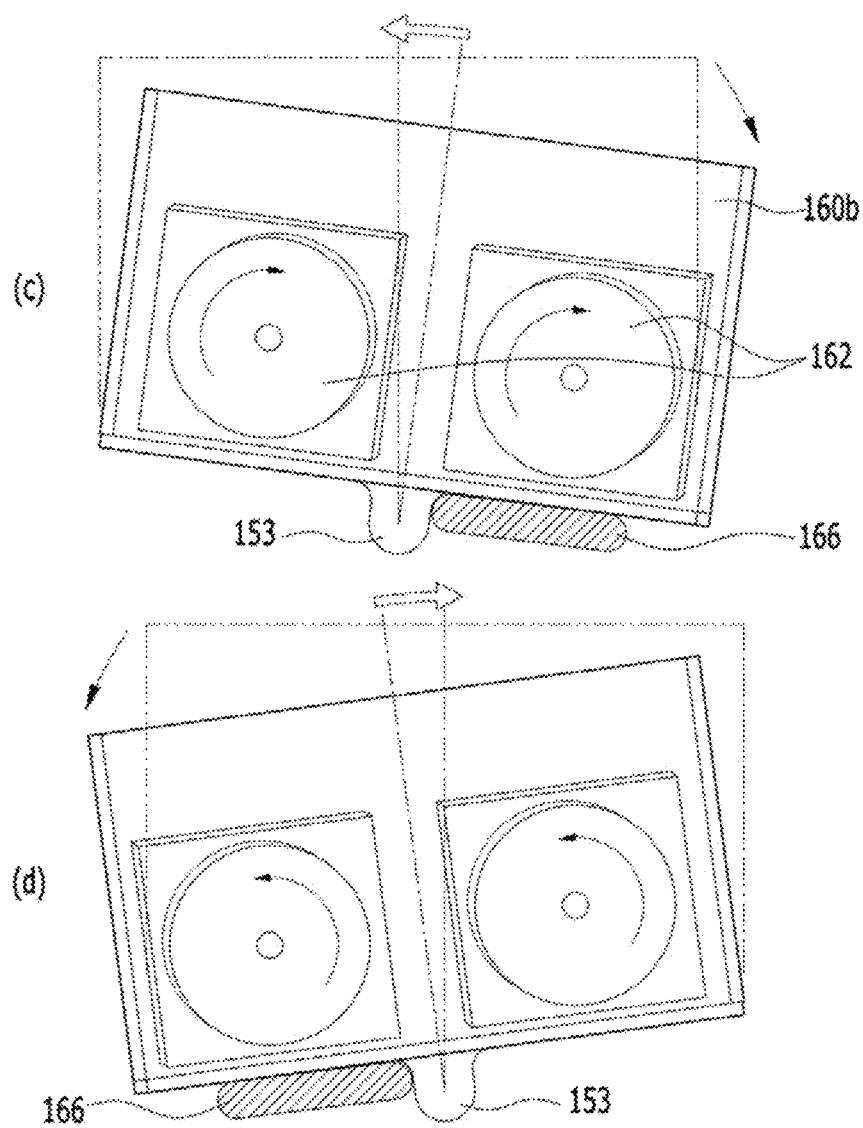

[FIG. 13]
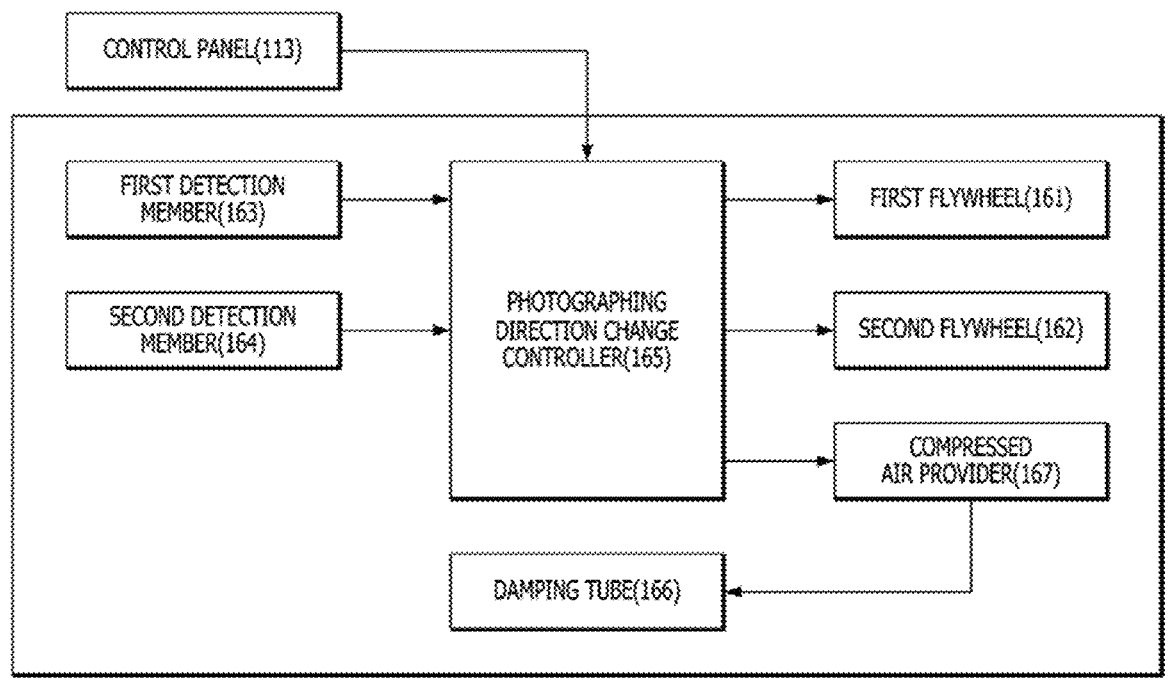

PORTABLE X-RAY DEVICE DRIVEN BY PFC-BASED INVERTER

CROSS REFERENCE TO RELATED APPLICATIONS

This application claims priority to Korean Patent Application No. 10-2022-0148437, filed on Nov. 9, 2022, the disclosures of which are incorporated by reference herein their entireties

FIELD OF THE INVENTION

The present invention relates to an X-ray device powered by a power factor correction (PFC)-based inverter, and more particularly, to a portable X-ray device with a portable structure.

Discussion of Related Art

X-ray imaging devices are widely used today in the medical field as devices for acquiring images of the inside of the human body.

As shown in FIG. 1, the X-ray imaging device according to the related art has a large volume and weight in terms of its structural aspect, and thus the X-ray imaging device is installed in an imaging room. Thus, the X-ray imaging device according to the related art has a problem in that it is very difficult to image patients with mobility difficulties.

In order to solve the above problem, a technology has been developed to change an installation location of the X-ray imaging device by attaching a transportation device to the X-ray imaging device.

Among X-ray imaging devices, portable X-ray imaging devices are especially popular for moving between hospital rooms, at home, and in emergency clinics due to their convenience of use. These devices are devices for acquiring an X-ray image of a subject by emitting X-rays toward the subject in a state in which an X-ray detector is disposed behind the subject.

However, the existing portable X-ray imaging devices only have photographing functions, leading to inconvenience. That is, because separate storage media or computers connected to a network are required in order to transmit images photographed through the portable X-ray imaging devices, there are many limitations in utilizing photographing information. In addition, since the portable X-ray imaging devices are moved and used in random places rather than in designated places, it is difficult to determine physical states of the portable X-ray imaging devices in the places where the portable X-ray imaging devices are being used and there is no way to control the portable X-ray imaging devices.

In addition, since the portable X-ray imaging device according to the related art has a structure that cannot receive good quality power, there is a problem in that it is difficult to acquire a high-quality X-ray imaging result.

Therefore, there is a need for a technology capable of solving the above problems according to the related art.

RELATED ART DOCUMENT

Patent Document (Patent Document 1) Korean Registered Patent No. 10-0935203 (registered on Dec. 24, 2009)

SUMMARY OF THE INVENTION

The present invention is directed to providing a portable X-ray device in which a power factor correction (PFC)-based inverter may be reliably applied to an X-ray device with a portable structure and which has a structure that may be carried and operated easily and safely.

According to an aspect of the present invention, there is provided a portable X-ray device including a body in which a plurality of wheels are mounted on a lower surface, an input/output device which extends from an installation ground to a predetermined height and outputs data acquired from an X-ray photographing part is mounted on one side, and a handle with a structure gripped by a hand of a user is mounted on one side: a variable support which is mounted on an upper portion of the body by a hinge structure and includes a plurality of hinge engagement structures that extend to one side by a predetermined length and allow an extension length and an angle to be changed: an X-ray photographing part which is mounted on one end portion of the variable support and has a structure which is engaged by the hinge engagement structure capable of changing an X-ray photographing direction according to an intent of the user and which is driven by a control signal input from a control panel mounted on one side to photograph an X-ray image of a photographing target: and a power supply mounted inside the body and provided with a PFC-based inverter configured to remove noise from applied commercial AC power, rectify the AC power, output a high DC voltage with a predetermined value through PFC, and provide the high DC voltage to the X-ray photographing part.

The power supply may include a filter configured to remove noise from the applied commercial AC power, a standby power supply connected to the filter to supply standby power, the PFC-based inverter connected to the filter and the standby power supply and configured to rectify the commercial AC power from which the noise is removed and output a high DC voltage with a predetermined value through PFC, a switching mode power supply (SMPS) connected to the PFC-based inverter and configured to receive the high DC voltage from the PFC-based inverter, convert the high DC voltage into low DC voltages with one or more values required for the X-ray photographing part, and output the low DC voltages, and an inverter, which drives X-ray photographing, connected to the PFC-based inverter and configured to receive the high DC voltage from the PFC-based inverter, convert the high DC voltage into a driving voltage for driving the X-ray photographing part, and output the driving voltage.

The variable support may include a first extension arm which is mounted on a first hinge structure at the upper portion of the body to be pivoted by a predetermined angle in a vertical direction and has a structure extending from the hinge structure to one side by a predetermined length, a second extension arm which is mounted on one end portion of the first extension arm to be pivoted by a predetermined angle by a first hinge engagement structure and has a structure extending from the first hinge engagement structure to one side by a predetermined length, a third extension arm which is mounted on one end of the second extension arm by a second hinge engagement structure to be pivoted by a predetermined angle about a pivoting axis in the extension direction of the second extension arm and has a structure extending from the second hinge engagement structure to one side by a predetermined length, a fourth extension arm which is mounted on a second hinge structure at one lower side of the body to be pivoted by a predetermined angle in the vertical direction and has a structure which extends to one side and is hinge-coupled to the first hinge engagement structure to fix a pivoting position of the first extension arm, and a third hinge engagement structure mounted on one end portion of the third extension arm (123) and configured to change the X-ray photographing direction of the X-ray photographing part (130).

The portable X-ray device may further include a photography housing which is engaged with one end portion of the variable support by the hinge engagement structure, is mounted in a structure that surrounds the X-ray photographing part, and has a rectangular parallelepiped structure which includes side walls in a direction perpendicular to a ground and changes an X-ray photographing direction by mounting the X-ray photographing part thereinside, a first flywheel mounted inside a first side wall of the photography housing and mounted to rotate in a direction parallel to a surface of the first side wall, a second flywheel mounted inside a second side wall orthogonal to the first side wall of the photography housing and mounted to rotate in a direction parallel to a surface of the second side wall, a first detection member mounted inside the first side wall and mounted adjacent to a rotation axis of the first flywheel to detect a rotation angle of the first side wall in real time and transmit the rotation angle to a controller, a second detection member mounted inside the second side wall and mounted adjacent to a rotation axis of the second flywheel to detect a rotation angle of the second side wall in real time and transmit the rotation angle to the controller, and a photographing direction change controller which is mounted inside the photography housing and configured to drive the first flywheel and the second flywheel in response to a control signal input from then input/output device of the body and change an engagement direction and an angle of the photography housing based on the hinge engagement structure to control the X-ray photographing direction to be changed and maintained.

The portable X-ray device may further include a damping tube which is mounted adjacent to the hinge engagement structure of the photography housing and has a structure that expands due to compressed air supplied from a compressed air provider to surround the hinge engagement structure and limiting a direction change of the photography housing, and the compressed air provider mounted adjacent to the hinge engagement structure of the photography housing and configured to operate in response to a control signal from the photographing direction change controller to inject compressed air into the damping tube.

In this case, the photographing direction change controller drives the first flywheel and the second flywheel according to a photographing direction setting of the X-ray photographing part input from the input/output device, changes the engagement direction and the angle of the photography housing, operates the compressed air provider to expand the damping tube, and controls the engagement direction and the angle of the photography housing to be fixed.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which:

FIG. 1 is a photograph showing an X-ray imaging device according to the related art:

FIG. 2 is a photograph showing a portable X-ray device according to one embodiment of the present invention:

FIG. 3 is a block diagram illustrating a power supply of the portable X-ray device according to one embodiment of the present invention:

FIG. 4 is a front view illustrating the portable X-ray device shown in FIG. 2:

FIG. 5 is a front view illustrating an operating state of a variable support of the portable X-ray device shown in FIG. 4:

FIG. 6 is a front view illustrating the operating state of the variable support of the portable X-ray device shown in FIG. 4:

FIG. 7 is a longitudinal cross-sectional view illustrating a damping tube and a compressed air provider mounted adjacent to a third hinge engagement structure according to another embodiment of the present invention:

FIG. 8 is a cross-sectional view along line A-A' of FIG. 7;

FIG. 9 shows longitudinal cross-sectional views illustrating a state of the damping tube driven as an angle of a third extension arm is changed by the third hinge engagement structure shown in FIG. 7:

FIG. 10 is a perspective view illustrating a first flywheel and a second flywheel mounted on a photography housing according to another embodiment of the present invention:

FIG. 11 is a front schematic diagram illustrating a state in which the first flywheel installed on a first side wall of the photography housing shown in FIG. 10 is rotated in a specific direction to change an inclination of the first side wall around the third hinge engagement structure;

FIG. 12 is a front schematic diagram illustrating a state in which the second flywheel installed on a second side wall of the photography housing shown in FIG. 10 is rotated in a specific direction to change an inclination of the second side wall around the third hinge engagement structure; and FIG. 13 is a control schematic diagram illustrating a control flow for controlling a photographing direction of the photography housing according to another embodiment of the present invention.

DETAILED DESCRIPTION OF EXEMPLARY EMBODIMENTS

Hereinafter, exemplary embodiments of the present invention will be described in detail with reference to the accompanying drawings. Prior to description, the terms or words used in the present specification and the appended claims should not be construed as being limited to ordinary or dictionary meanings and should be construed with meanings and concepts consistent with the technical idea of the present invention.

Throughout the present specification, when a first member is referred to as being "on" a second member, this includes not only when the first member is in contact with the second member, but also when a third member is present between the first member and the second member. Throughout the present specification, when a part is referred to as "including" a component, this means that the part can include other elements, rather than excluding any other components unless specifically stated otherwise.

FIG. 2 is a photograph showing a portable X-ray device according to one embodiment of the present invention, and FIG. 3 is a block diagram illustrating a power supply of the portable X-ray device according to one embodiment of the present invention.

Referring to these drawings, the portable X-ray device 100 according to the present embodiment includes a body 110 of a specific structure, a variable support 120, an X-ray photographing part 130 and a power supply 140 and may stably provide a high DC voltage generated by a power factor correction (PFC)-based inverter as a DC voltage required for the X-ray photographing part 130 so that stable operation of the portable X-ray device can be ensured.

Hereinafter, each component constituting the portable X-ray device 100 according to the present embodiment will be described in detail with reference to the accompanying drawings.

FIG. 4 is a front view illustrating the portable X-ray device shown in FIG. 2, FIG. 5 is a front view illustrating an operating state of a variable support of the portable X-ray device shown in FIG. 4, and FIG. 6 is a front view illustrating an operating state of a variable support of the portable X-ray device shown in FIG. 4.

Referring to FIGS. 2 to 6, a body 110 of the portable X-ray device 100 has a structure in which a plurality of wheels 111 are installed on a lower surface, an input/output device 112 extending from an installation ground to a predetermined height and outputting data acquired from the X-ray photographing part 130 is mounted at one side, and a handle 114 having a structure held by a hand of a user is mounted at one side.

The input/output device 112 may be an electronic device or a laptop computer, which is easily detachable, attachable, and portable.

The variable support 120 according to the present embodiment is a component mounted on an upper portion of the body 110 by a hinge structure 115 and has a structure including a plurality of hinge engagement structures 150 which extend to one side by a predetermined length and of which an extension length and an angle can be changed.

The X-ray photographing part 130 according to the present embodiment is a component mounted on one end portion of the variable support 120 and has a structure which is engaged by the hinge engagement structure 150 capable of changing an X-ray photographing direction according to an intent of the user and which is driven by a control signal input from a control panel 131 mounted on one side to photograph an X-ray image of a photographing target. The control panel 131 may be formed of a laptop computer and an optical drive cover.

The power supply 140 according to the present embodiment is a component mounted inside the body 110 and includes a PFC-based inverter 141 for removing noise from applied commercial AC power, rectifying the AC power, outputting a high DC voltage with a predetermined value through PFC, and providing the high DC voltage to the X-ray photographing part 130.

In addition, the power supply 140 has a structure serving as a detector holder and is provided with a connection terminal, to which a power input cable is connected, on one side thereof. In this case, the power input cable is connected to a wall power source and an inlet of a mobile cart to supply power to the mobile cart (main body), and the power is distributed inside the detector holder (cassette tray) and supplied to the X-ray photographing part 130 through a cable (power+signal) added to the second extension arm 122 of the variable support 120.

Specifically, as shown in FIG. 3, the power supply 140 may be a component including a filter 142 performing a specific function, a standby power supply 143, a PFC-based inverter 141, a switching mode power supply (SMPS) 144, and an inverter 145 for driving X-ray photographing.

The filter 142 of the power supply 140 may remove noise from applied commercial AC power. The standby power supply 143 may be connected to the filter 142 and may supply standby power. The PFC-based inverter 141 is connected to the filter 142 and the standby power supply 143 and may rectify the commercial AC power from which noise is removed and output a high DC voltage with a predetermined value through PFC. The SMPS 144 is connected to the PFC-based inverter 141 and may receive the high DC voltage from the PFC-based inverter 141, convert the high DC voltage into low DC voltages with one or more values required for the X-ray photographing part 130, and output the low DC voltages. In this case, the inverter 145 for driving X-ray photographing is connected to the PFC-based inverter 141 and may receive the high DC voltage from the PFC-based inverter 141, convert the high DC voltage into a driving voltage for driving the X-ray photographing part 130, and output the driving voltage.

As described above, according to the portable X-ray device of the present invention, the body 110 of a specific structure, the variable support 120, the X-ray photographing part 130, and the power supply 140 are provided, and thus the high DC voltage generated by the PFC-based inverter may be stably provided as the DC voltage required for the X-ray photographing part 130 so that the portable X-ray device capable of ensuring stable operation may be provided.

Meanwhile, as shown in FIGS. 4 to 6, the variable support 120 according to the present embodiment may include a first extension arm 121, a second extension arm 122, a third extension arm 123, and a fourth extension arm 124, which each have a specific structure.

Specifically, the first extension arm 121 is a component mounted on a first hinge structure 115a at the upper portion of the body 110 to be pivoted by a predetermined angle in a vertical direction and has a structure extending from the hinge structure 115 to one side by a predetermined length. The second extension arm 122 is a component mounted on one end of the first extension arm 121 to be pivoted by a predetermined angle by a first hinge engagement structure 151 and has a structure extending from the first hinge engagement structure 151 to one side by a predetermined length. The third extension arm 123 is a component mounted on one end of the second extension arm 122 by a second hinge engagement structure 152 to be pivoted by a predetermined angle about a rotation axis in the extension direction of the second extension arm 122 and has a structure extending from the second hinge engagement structure 152 to one side by a predetermined length. The fourth extension arm 124 is a component mounted on a second hinge structure 115b at one lower side of the body 110 to be pivoted by a predetermined angle in the vertical direction and has a structure which extends to one side and is hinge-coupled to the first hinge engagement structure 151 to fix a pivoting position of the first extension arm 121. In this case, a third hinge engagement structure 153 has a structure mounted on one end portion of the third extension arm 123 to allow an X-ray photographing direction of the X-ray photographing part 130 to be changed.

In this case, according to the portable X-ray device of the present invention, the variable support 120 which includes the first extension arm 121, the second extension arm 122, the third extension arm 123, the fourth extension arm 124, which each have a specific structure, the first hinge structure 115a, the second hinge structure 115b, the first hinge engagement structure 151, the second hinge engagement structure 152, and the third hinge engagement structure 153 are provided so that the portable X-ray device in which the position and direction of the X-ray photographing part 130 can be freely and stably changed according to an intent of the user may be provided.

FIG. 7 is a longitudinal cross-sectional view illustrating a damping tube and a compressed air provider mounted adjacent to a third hinge engagement structure according to another embodiment of the present invention, FIG. 8 is a cross-sectional view along line A-A' of FIG. 7, and FIG. 9 shows longitudinal cross-sectional views illustrating a state of the damping tube driven as an angle of a third extension arm is changed by the third hinge engagement structure shown in FIG. 7. In addition, FIG. 10 is a perspective view illustrating a first flywheel and a second flywheel mounted on a photography housing according to another embodiment of the present invention, FIG. 11 is a front schematic diagram illustrating a state in which the first flywheel installed on a first side wall of the photography housing shown in FIG. 10 is rotated in a specific direction to change an inclination of the first side wall around the third hinge engagement structure, and FIG. 12 is a front schematic diagram illustrating a state in which the second flywheel installed on a second side wall of the photography housing shown in FIG. 10 is rotated in a specific direction to change an inclination of the second side wall around the third hinge engagement structure. In addition, FIG. 13 is a control schematic diagram illustrating a control flow for controlling a photographing direction of the photography housing according to another embodiment of the present invention.

Referring to these drawings, the portable X-ray device 100 according to the present embodiment includes a photography housing 160 of a specific structure, a first flywheel 161, a second flywheel 162, a first detection member 163, a second detection member 164, a photographing direction change controller 165, a damping tube 166, and a compressed air provider 167.

Specifically, the photography housing 160 is a component engaged with one end of the variable support 120 by a hinge engagement structure 150, is mounted in a structure that surrounds an X-ray photographing part 130, and has a rectangular parallelepiped structure which includes side walls in the direction perpendicular to the ground and changes an X-ray photographing direction by the X-ray photographing part 130 being mounted thereinside. The first flywheel 161 is a component mounted inside a first side wall 160*a* of the photography housing 160 and mounted to rotate in a direction parallel to a surface of the first side wall 160*a*. The second flywheel 162 is a component mounted inside a second side wall 160*b* orthogonal to the first side wall 160*a* of the photography housing 160 and mounted to rotate in a direction parallel to a surface of the second side wall 160*b*. The first detection member 163 is a component mounted inside the first side wall 160*a* and may be mounted adjacent to a rotation axis of the first flywheel 161 and detect a rotation angle of the first side wall 160*a* in real time to transmit the rotation angle to a controller. The second detection member 164 is a component mounted inside the second side wall 160*b* and may be mounted adjacent to a rotation axis of the second flywheel 162 and detect a rotation angle of the second side wall 160*b* in real time to transmit the rotation angle to the controller. In addition, the photographing direction change controller 165 is a component mounted inside the photography housing 160 and may drive the first flywheel 161 and the second flywheel 162 in response to a control signal input from an input/output device 112 of a body 110 and change an engagement direction and an angle of the photography housing 160 based on the hinge engagement structure 150 to control the X-ray photographing direction to be changed and maintained.

The damping tube 166 according to the present embodiment is a component mounted adjacent to the hinge engagement structure 150 of the photography housing 160 and has a structure that expands due to compressed air supplied from the compressed air provider 167 to surround the hinge engagement structure 150 and limits a direction change of the photography housing 160. In addition, the compressed air provider 167 is a component mounted adjacent to the hinge engagement structure 150 of the photography housing 160 and may operate in response to a control signal from the photographing direction change controller 165 to inject compressed air into the damping tube 166.

In this case, the photographing direction change controller 165 according to the present embodiment may drive the first flywheel 161 and the second flywheel 162 according to a photographing direction setting of the X-ray photographing part 130 input from the input/output device 112, change the engagement direction and the angle of the photography housing 160, operate the compressed air provider 167 to expand the damping tube 166, and control the engagement direction and the angle of the photography housing 160 to be fixed.

In this case, according to the portable X-ray device of the present invention, the photography housing 160 of a specific structure, the first flywheel 161, the second flywheel 162, the first detection member 163, the second detection member 164, the damping tube 166, the compressed air provider 167, and the photographing direction change controller 165 are provided, and thus the photographing direction of the X-ray photographing part 130 input from the input/output device 112 may be easily and accurately set and fixed by the user. Therefore, the portable X-ray device capable of ensuring accuracy of an X-ray imaging result may be provided.

As described above, according to a portable X-ray device of the present invention, a body of a specific structure, a variable support, an X-ray photographing part, and a power supply are provided, and thus a high DC voltage generated by a PFC-based inverter can be stably provided as a DC voltage required for the X-ray photographing part so that the portable X-ray device capable of ensuring stable operation can be provided.

In addition, according to the portable X-ray device of the present invention, the variable support which includes a first extension arm, a second extension arm, a third extension arm, and a fourth extension arm, which each have a specific structure, and a first hinge structure, a second hinge structure, a first hinge engagement structure, a second hinge engagement structure, and a third hinge engagement structure is provided so that the portable X-ray device capable of freely and stably changing a position and direction of the X-ray photographing part according to an intent of the user can be provided.

In addition, according to the portable X-ray device of the present invention, a photography housing of a specific structure, a first flywheel, a second flywheel, a first detection member, a second detection member, a damping tube, a compressed air provider, and a photographing direction change controller are provided, and thus the photographing direction of the X-ray photographing part input from a control panel can be easily and accurately set and fixed by the user. Therefore, the portable X-ray device capable of ensuring accuracy of an X-ray imaging result can be provided.

In the above detailed description of the present invention, only specific embodiments thereof are described. However, it should be understood that the present invention is not limited to the particular form described in the detailed description, but rather is understood to include all modifications, equivalents, and substitutes within the spirit and scope of the present invention as defined by the appended claims.

That is, the present invention is not limited to the specific embodiments and the descriptions, and various modifications can be made by those skilled in the art without departing from the gist of the present invention as claimed in the appended claims, and such modifications fall within the scope of protection of the present invention.

The invention claimed is:

1. A portable X-ray device comprising:
a body (110) in which a plurality of wheels (111) are mounted on a lower surface, an input/output device (112) which extends from an installation ground to a predetermined height and outputs data acquired from an X-ray photographing part is mounted on one side, and a handle (114) with a structure gripped by a hand of a user is mounted on one side;
a variable support (120) which is mounted on an upper portion of the body (110) by a hinge structure (115) and includes a plurality of hinge engagement structures (150) that extend to one side by a predetermined length and allow an extension length and an angle to be changed;
an X-ray photographing part (130) which is mounted on one end portion of the variable support (120) and has a structure which is engaged by the hinge engagement structure (150) that allows an X-ray photographing direction to be changed according to an intent of the user and which is driven by a control signal input from a control panel (131) mounted on one side to photograph an X-ray image of a photographing target;
a power supply (140) mounted inside the body (110) and provided with a power factor correction (PFC)-based inverter (141) configured to remove noise from applied commercial AC power, rectify the AC power, output a high DC voltage with a predetermined value through PFC, and provide the high DC voltage to the X-ray photographing part (130);
a photography housing 160 which is engaged with one end portion of the variable support (120) by the hinge engagement structure (150), is mounted in a structure that surrounds the X-ray photographing part (130), and has a rectangular parallelepiped structure which includes side walls in a direction perpendicular to a ground and changes an X-ray photographing direction by mounting the X-ray photographing part (130) thereinside;
a first flywheel (161) mounted inside a first side wall (160a) of the photography housing (160) and mounted to rotate in a direction parallel to a surface of the first side wall (160a);
a second flywheel (162) mounted inside a second side wall (160b) orthogonal to the first side wall (160a) of the photography housing (160) and mounted to rotate in a direction parallel to a surface of the second side wall (160b);
a first detection member (163) mounted inside the first side wall (160a) and mounted adjacent to a rotation axis of the first flywheel (161) to detect a rotation angle of the first side wall (160a) in real time and transmit the rotation angle to a controller;
a second detection member (164) mounted inside the second side wall (160b) and mounted adjacent to a rotation axis of the second flywheel (162) to detect a rotation angle of the second side wall (160b) in real time and transmit the rotation angle to the controller; and
a photographing direction change controller (165) mounted inside the photography housing (160) and configured to drive the first flywheel (161) and the second flywheel (162) in response to a control signal input from an input/output device (112) and change an engagement direction and an angle of the photography housing (160) based on the hinge engagement structure (150) to control the X-ray photographing direction to be changed and maintained,
wherein the power supply (140) includes:
a filter (142) configured to remove noise from the applied commercial AC power;
a standby power supply (143) connected to the filter (142) to supply standby power;
the PFC-based inverter (141) connected to the filter (142) and the standby power supply (143) and configured to rectify the commercial AC power from which the noise is removed and output a high DC voltage with a predetermined value through PFC;
a switching mode power supply (SMPS) (144) connected to the PFC-based inverter (141) and configured to receive the high DC voltage from the PFC-based inverter (141), convert the high DC voltage into low DC voltages with one or more values required for the X-ray photographing part (130), and output the low DC voltages; and
an inverter (145), which drives X-ray photographing, connected to the PFC-based inverter (141) and configured to receive the high DC voltage from the PFC-based inverter (141), convert the high DC voltage into a driving voltage for driving the X-ray photographing part (130), and output the driving voltage.

2. The portable X-ray device of claim 1, wherein the variable support (120) includes:
a first extension arm (121) which is mounted on a first hinge structure (115a) at the upper portion of the body (110) to be pivoted by a predetermined angle in a vertical direction and has a structure extending from the hinge structure (115) to one side by a predetermined length;
a second extension arm (122) which is mounted on one end portion of the first extension arm (121) to be pivoted by a predetermined angle by a first hinge engagement structure (151) and has a structure extending from the first hinge engagement structure (151) to one side by a predetermined length;
a third extension arm (123) which is mounted on one end of the second extension arm (122) by a second hinge engagement structure (152) to be pivoted by a predetermined angle about a pivoting axis in the extension direction of the second extension arm (122) and has a structure extending from the second hinge engagement structure (152) to one side by a predetermined length;
a fourth extension arm (124) which is mounted on a second hinge structure (115b) at one lower side of the body (110) to be pivoted by a predetermined angle in the vertical direction and has a structure which extends to one side and is hinge-coupled to the first hinge engagement structure (151) to fix a pivoting position of the first extension arm (121); and
a third hinge engagement structure (153) mounted on one end portion of the third extension arm (123) and configured to change the X-ray photographing direction of the X-ray photographing part (130).

3. The portable X-ray device of claim 1, further comprising:
- a damping tube (166) which is mounted adjacent to the hinge engagement structure (150) of the photography housing (160) and has a structure that expands due to compressed air supplied from a compressed air provider (167) to surround the hinge engagement structure (150) and limiting a direction change of the photography housing (160); and
- the compressed air provider (167) mounted adjacent to the hinge engagement structure (150) of the photography housing (160) and configured to operate in response to a control signal from the photographing direction change controller (165) to inject compressed air into the damping tube (166),
- wherein the photographing direction change controller (165) drives the first flywheel (161) and the second flywheel (162) according to a photographing direction setting of the X-ray photographing part (130) input from the input/output device (112), changes the engagement direction and the angle of the photography housing (160), operates the compressed air provider (167) to expand the damping tube (166), and controls the engagement direction and the angle of the photography housing (160) to be fixed.

\* \* \* \* \*